United States Patent [19]

Blumenthal et al.

[11] 4,349,353

[45] Sep. 14, 1982

[54] FRYING OIL EVALUATOR METHOD AND COMPOSITION

[75] Inventors: Michael M. Blumenthal, Metuchen, N.J.; Jerry R. Stockler, Wantagh, N.Y.

[73] Assignee: Oil Process Systems, Inc., Allentown, Pa.

[21] Appl. No.: 305,841

[22] Filed: Sep. 25, 1981

[51] Int. Cl.$^3$ .................... G01N 33/02; G01N 33/28
[52] U.S. Cl. .................... 23/230 R; 23/230 M; 422/61; 252/408
[58] Field of Search .................... 23/230 M, 230 R; 422/61; 252/408

[56] References Cited

U.S. PATENT DOCUMENTS 3,682,597  8/1972  Husch .................... 422/61 X

OTHER PUBLICATIONS

A.O.C.S. Recommended Practice cc 17-79.
Nelson, R. M., Jour. of the Amer. Oil Chem. Soc., "Titrimetric Determination of Soap in Refined Vegetable Oil", Jun. 1973, pp. 207-209.
Blumenthal, M. M., "Frying Fat: Fact vs. Fancies", A bulletin from Oil Process Systems, Inc.

*Primary Examiner*—Ronald E. Serwin
*Attorney, Agent, or Firm*—Lerner, David, Littenberg & Samuel

[57] ABSTRACT

A method and composition for a determination of alkaline materials such as soap in fat are disclosed. In the disclosed method, a predetermined amount of a test solution containing a solvent and a dye is mixed with fat; the fat and test solution are allowed to separate into two phases; and the color developed in one of the phases is compared with a known standard to determine the amount of alkaline materials in the fat. A test solution and test kit for performing the method are also disclosed.

15 Claims, No Drawings

FRYING OIL EVALUATOR METHOD AND COMPOSITION

BACKGROUND OF THE INVENTION

The present invention relates to a method and composition for determining contaminants in fats and oils. More specifically, the present invention relates to an easy to use, inexpensive method and composition to evaluate the quality of fats and oils, especially as regards soap and other alkaline substance levels.

One of the factors determining the cooking quality of used frying fats and oils is the amount of alkaline substances, including soaps, initially present and accumulated in the fat or oil during cooking. Normally, the more alkaline substances in the fat or oil, the worse the cooking properties of the fat or oil. However, for a restaurant or a fast-food outlet, it is difficult to evaluate the quality of the used cooking oil on the premises, other than by merely looking at its color, smelling its odor, and/or observing its frying properties.

The American Oil Chemists' Society (A.O.C.S.) has set up certain standard methods for evaluating the quality of freshly refined cooking oil, including the amount of "soaps" in the fresh oil. Presently, the amount of soaps in freshly refined fat and oil is determined by procedures which are both relatively complex and require substantial apparatus and a trained operator. For example, the A.O.C.S. Recommended Practice Cc 17-79 requires a titration to determine the amount of soaps in the fresh oil. Accordingly, this method requires equipment and solutions not normally found in restaurants and fast-food outlets. Moreover, the procedure is not recommended for use with used cooking oils.

Others have developed standard methods for determining the quality characteristics of used cooking oils by determining, among other things, free fatty acid content, color, odor, etc. However, while the amounts of alkaline substances in used cooking oil have previously been determined, until recently, there has not been any real interest in measuring the amount of "soaps" in used cooking oil either on the industrial level or on the restaurant or fast-food outlet level, since "soaps" were not considered important in determining the quality of the oil. In addition, such facilities did not have the apparatus required to make such determinations. Moreover, as far as applicants know, no one has developed standards or test procedures for determining the quality characteristics of used cooking oils in terms of the alkaline substances therein, including soaps. As is pointed out in U.S. application Ser. No. 069,238 filed Aug. 23, 1979 of Bernard Friedman, such alkaline substances have been found to contribute to the loss of desirable cooking properties in the used cooking oil. Thus, it would be very desirable to have a quick, easy and inexpensive way to measure the amounts of such alkaline substances in used cooking oil.

The present applicants have found in performing the above-mentioned A.O.C.S. Recommended Method that when higher levels of alkaline substances are present as in used fats, the recommended procedure has a number of disadvantages. Two such disadvantages are (1) the formation of emulsions, and (2) lack of correlation of known high amounts of soaps in fats (prepared by adding known amounts of soaps to soap-free fats) and the results found for such fats by the Recommended Method. Also, the method is specifically recommended for vegetable oils.

Thus, it would also be desirable to provide a method by which soap levels in various types of fats could be determined regardless of their origin and by which higher levels of soap concentrations can be more accurately measured, which high levels correlate to a fry chef's judgment of when a fat or oil is no longer suitable for frying.

SUMMARY OF THE INVENTION

It has now been found that, in accordance with the present invention, a quick, easy, and inexpensive method can be provided for determining the amount of alkaline substances in used cooking fat. In the method of the invention, a predetermined amount of test solution is mixed with a predetermined amount of fat. The test solution comprises a pH indicator dye having a visible color change in the pH range of from about 2.5 to about 7.0 and a solvent in which the dye is soluble and with which the fat is immiscible. The dye and solvent are present in the test solution in amounts effective to provide a visible color change which depends upon the amount of alkaline substances, e.g., soaps, in the fat. The pH of the test solution is such that the color of the test solution prior to the mixing step corresponds to the color of the dye at the lower end of the color change range for the dye. After mixing, the fat and test solution are allowed to separate into a solvent phase and a fat phase. The amount of alkaline substances in the fat is then determined from the color developed in the solvent phase by comparing the developed color to a known standard, e.g., visually, in a colorimeter or in a spectrophotometer. Preferably, the color developed in the solvent phase is compared with a set of colors standardized so that each color corresponds to a specified amount of soap and/or other alkaline substances in the predetermined amount of fat. In this way, the amount of soap and/or other alkaline substances in the fat can be determined on-site by restaurants and fast-food outlets, etc. It should be pointed out, however, that the method can also be used industrially or even to determine the amounts of soaps in "freshly refined" oils and fat being considered for cooking purposes.

Another embodiment of the present invention comprises a test kit for determining the amount of soaps or other alkaline substances in fat. The test kit comprises a test solution and a set of standardized colors. The test solution is the same as the test solution described above. The set of colors is standardized so that each color corresponds to a color developed when a predetermined amount of test solution is mixed with a predetermined amount of fat containing a specified amount of alkaline substances. The kit can also contain other apparatus for performing the method, such as test tubes, dispensing bottles, caps for the test tubes, droppers, ladles, test tube holders, etc.

The method and test kit of the present invention have a number of advantages which make them very useful to restaurants, fast-food outlets, and large scale frying operations, etc. The method and test kits are field usable. They provide a single component test solution requiring no pre-mixing or post mixing of reagents by the user. They provide a fast chemical reaction with permanent results, i.e., the color remains in the solvent phase for a relatively long period of time, not requiring immediate determination. Moreover, the colors developed are distinct so as to allow rapid decision on the quality of the oil. The method and test kit of the present invention also require very small amounts of fat compared with the A.O.C.S. or similar procedures. Thus, for the restaurant or fast-food outlet owner, the method and test kit is simple to use and can be performed by non-sophisticated personnel with a minimum of instruction.

DETAILED DESCRIPTION OF THE INVENTION

The method and test kit in accordance with the present invention employ pH indicator dye which has a visible color change in the pH range of from about 2.5 to about 7.0. Preferably, the dye has a color change in the pH range of from about 3.0 to about 5.0. The selection of the specific dye to be employed in the test solution depends on the nature of the solvent system and the suspected level of contamination of alkaline substances in the used cooking fat or oil. The dye should be soluble in the solvent system and not react with or be displaced by the solvent system or fat. Examples of suitable dyes for use in the present invention include the following dyes having the pH color change range and color change indicated below:

| Dye | pH color change range | Color Change visible |
|---|---|---|
| Methyl yellow | 2.9–4.0 | red-yellow |
| Bromophenol blue | 3.0–4.6 | yellow-blue (purple) |
| Congo red | 3.0–5.0 | blue-red |
| Methyl orange | 3.1–4.4 | red-yellow |
| Brom-Chlorphenol blue | 3.2–4.8 | yellow-purple |
| Bromocresol green | 3.8–5.4 | yellow-blue |
| Bromocresol purple | 5.2–6.8 | yellow-purple |
| Chlorophenol red | 5.2–6.8 | yellow-red |

The test solution used in the present invention contains a sufficient amount of the dye so that, when a predetermined amount of the test solution is mixed with a predetermined amount of fat, a sufficient color development is obtained in the solvent phase to indicate the relative amount of soaps and/or other alkaline substances in the fat. The concentration of the dye is chosen so as to make simple the comparison of the color developed in the test solution with the standardized colors corresponding to normally expected concentrations of alkaline substances in used fat. Typically, the test solution contains from about 0.002 to about 0.015 parts by weight of dye per hundred parts by weight of the test solution. With bromophenol blue a typical desirable range has been found to be about 0.004 to about 0.008 parts by weight of dye per hundred parts by weight of the test solution.

In a preferred embodiment, a sufficient amount of the dye is included in the test solution so that when the predetermined amount of the test solution is mixed with the predetermined amount of the fat containing an amount of soaps and/or other alkaline substances making the fat unsuitable for further cooking use, a sufficient color development occurs so that a quick and easy determination can be made to discard such used fat or to treat it to remove alkaline substances.

The test solution used in the method and test kit of the present invention also includes a solvent in which the dye is soluble and with which the fat is immiscible. Preferably, the solvent system is a polar organic solvent and an aqueous liquid. Such a solvent system contains water and polar organic solvent in proportion to each other so as to extract the alkaline substances from the fat and so as to provide a solvent system immiscible with the fat. As mentioned above, the solvent system should also not react with or displace the dye. Examples of suitable polar organic solvents include acetone, propylene glycol, isopropyl alcohol, ethyl alcohol, and mixtures thereof.

The solvent is present in the test solution in combination with the dye in an amount effective to provide a visible color change when the test solution is mixed with a used fat having a characteristic amount of alkaline substances. By characteristic amount, we mean ranges of concentrations of alkaline substances that typically occur in used cooking fat. The visible color appears in the solvent phase above the fat phase after settling of the fat. Sufficient relative amounts of solvent and dye are present so as to provide the most clearly distinguishable range of colors corresponding to different concentrations of alkaline substances in the used fat. The relative amounts of solvent and dye are typically chosen to provide such results with expected concentrations of alkaline substances in used fat. The solvent obviously comprises most of the test solution except for the dye. However, it should be pointed out that other materials can be present in the test solution, such as materials to suppress foams, materials to enhance the separation of the fat phase from the solvent phase, materials to suppress solvation of unwanted substances into the solvent phase from the fat, and/or the residue of the materials used to adjust the pH of the test solution, e.g., residues from sodium hydroxide and hydrogen chloride solutions.

The pH of the test solution is adjusted, if necessary, so that the color of the test solution, to be mixed with the predetermined amount of fat, corresponds to the color of the dye at the lower end of the color change range for the dye. Thus, in this manner, when alkaline substances are extracted from the fat into the solvent phase, the pH of the solvent phase is increased and the dye changes color indicating the amount of alkaline substances so extracted. The pH can be adjusted in any conventional manner. Typically, weak sodium hydroxide solution and weak hydrogen chloride solution are used to adjust the pH.

The relative amounts of the test solution and fat that are employed in the method of the present invention depend upon a number of factors including the concentration of dye in the test solution, the expected level of alkaline substances in the fat, the dye composition itself, i.e., the color it develops in relationship to the amount of soaps or other alkaline substances, etc. Typically, the test solution is prepared so that it can be mixed in a 1:1 volume relationship with the fat sample such that typical ranges of soaps or other alkaline substances in such a predetermined amount of fat will provide a desired range of colors so that the amount of soaps or other alkaline substances in the fat can be visually determined. The test solution is preferably prepared so that, when the predetermined amount of the test solution is mixed with a predetermined amount of a fat containing an undesirably high level of soap or other alkaline substances rendering the fat unsuitable for further use in frying, the color change developed clearly indicates the fat as being so unsuitable.

In use, a predetermined amount of the test solution of the present invention is mixed with a predetermined amount of the fat sample containing an unknown amount of soap or other alkaline substances. The mixing normally takes place in a convenient container such as closed vessel, e.g., a closed test tube. The fat should be liquid, and if it is not, can be made liquid by immersion in a stream of hot running water or by any other suitable heating means. The mixture can be merely shaken and then allowed to separate into the solvent phase and the fat phase. The amount of the alkaline substances in the fat are thus determined from the color developed in the solvent phase by comparing the developed color to a known standard. The color also indicates the frying characteristics of the fat. For example, the color in the solvent phase can be compared with a set of colors standardized so that each color indicates a specific amount of alkaline substances in the predetermined amount of the fat. Also, the color comparison can be performed colorimetrically or spectrophotometrically by techniques well-known in the art.

The process of the present invention is normally performed under ambient conditions. However, any other process conditions can be used which do not change the color development obtained by the use of the predetermined amount of test solution and predetermined amount of fat containing an unknown amount of soaps or other alkaline substances. If a dye is employed which fluoresces in the desired pH range, illumination can be ultraviolet lights so that the color change can be made visible.

The test kit of the present invention includes the test solution and a set of standardized colors which can be used to compare to the color developed in the solvent phase and thus to determine the relative amount of soaps or other alkaline substances extracted from the predetermined amount of fat. The set of standardized colors can be prepared, for example, by performing the method of the present invention employing the predetermined amount of the test solution with a series of fat samples containing known amounts of soap as an example of alkaline substances. These known amounts of soap are selected to represent typical soap levels in used fat and include soap levels which would render the fat unsuitable for use in frying. The predetermined amounts of such fats containing known amounts of soap are then used in the method of the present invention and the colors corresponding to such known amounts of soap are allowed to develop in the solvent phase. These colors in the solvent phase corresponding to known amounts of soap in the predetermined amount of fat can either be used directly for the comparison or can be used to prepare a color chart, for example, either on a sheet of paper, in a series of solutions, or colored glasses or plastic, or on other media. In this manner, the relative amount of alkaline substances commonly expressed as "soap" in the unknown fat sample can be determined easily, inexpensively, and on site.

The test kit of the present invention can also include more than one test solution. The test kit could, for example, include three test solutions corresponding to three overlapping pH ranges correlating to lower levels of soap concentrations, intermediate levels of soap concentrations, and higher levels of soap concentrations. In this manner, wide variations in soap concentrations in fat can be determined by one kit. Moreover, the soap concentration in the fat could be bracketed by employing the various test solutions. This combination of test solutions would also make the test kit of the present invention suitable for use in quality control determinations or even research applications.

Conveniently, the test kit of the present invention is packaged to use polypropylene test tubes with screw caps of polyethylene as the mixing containers. Tall, narrow containers are preferred to observe the color reaction. If desired, lighting can be employed to pass through sample, e.g., fluorescent light by either transmission or reflection. Incandescent light or sunlight can also be employed. The observation of the color developed in the test solution can also be made by a colorimeter or a spectrophotometer as is well known in the art.

The test solution of the present invention can be prepared by any conventional means. For example, the desired amount of the dye can be mixed with the polar organic solvent. The desired amount of aqueous liquid, if employed, can be added and then the pH can be adjusted, for example, by using sodium hydroxide and/or hydrogen chloride solutions. The desired final concentration can be fixed by adding an appropriate amount of a polar organic solvent by techniques well-known in the art.

The alkaline substances determined by the method and test kit of the present invention include alkaline materials such as normally found in fats such as soaps. Additionally, alkaline substances can be introduced into used fat by the cooking of foods. The possible source of such alkaline substances could be leavening agents, amines from proteins in the food, etc. These alkaline substances apparently behave as surfactants or detergents in the fat and contribute to the degradation of the frying properties of the used oil. Typical concentrations of alkaline substances in used fat, of course, depend upon a large number of factors including the type of oil employed, replacement of used oil with makeup fresh oil, etc. Such typical concentrations of alkaline substances in used fat range from about 1 or 2 parts per million to several hundred parts per million.

In a preferred embodiment of the present invention, the test solution is comprised of dye in an amount effective to provide a visible color change when the test solution is mixed with a fat having a characteristic amount of alkaline substances and of water and polar organic solvent in proportion to each other so as to extract the alkaline substances from the fat and so as to provide a solvent system immiscible with the fat.

In another preferred embodiment of the present invention, the test solution is comprised of from about 0.004 to about 0.008 parts by weight of bromophenol blue per hundred parts by weight of the test solution, from about 2 to about 25 parts by weight of water per hundred parts of the test solution, and from about 75 to about 98 parts by weight of acetone per hundred parts of the test solution. Particularly good results have been obtained by a test solution comprised of the following relative amounts of dye, acetone, and water: about 0.04 grams of bromophenol blue, about 75 milliliters of water, and the remainder being acetone and small amounts of sodium hydroxide solution and hydrogen chloride solution to adjust the pH as described above.

The following examples are intended to illustrate, but not to limit, the present invention.

EXAMPLE 1

A test solution is prepared by mixing 0.0400 grams of bromophenol blue with about 750 to 800 milliliters of acetone. 75 milliliters of water are added and the pH of the solution is adjusted so that the yellow color of the bromophenol blue dye corresponding to the lower end of the color change range (pH approximately 3.0) for bromophenol blue is obtained. In the present instance, this required 1.10 milliliters of 0.1 N sodium hydroxide and 5 drops of 0.01 N hydrogen chloride. Acetone was then added to bring the solution up to 1000 milliliters.

A series of fat samples were prepared containing known concentrations of soap. Five milliliters of each of such fat samples were mixed in a test tube with five milliliters of the above-described test solution. The test tubes were stoppered and shaken and the phases were allowed to separate. A series of test tube samples were thus obtained with the solvent phase showing a progressive increase in color from yellow to green and blue color indicating the relative increase in the amount of soap in the known samples.

Five milliliters of a fat sample containing an unknown amount of soap is then mixed in the same manner with five milliliters of the test solution. The test tube is shaken, the phases allowed to separate, and the color developed in the solvent phase is compared with the colors in the solvent phase from the standardization procedure described above to determine the amount of soap in the unknown fat sample.

The results of these tests were then compared to the actual soap (or other alkaline materials) as determined by the A.O.C.S. titration method. The following (rough) color/ppm soap (or other alkaline material) correlation was made.

| Color | ppm |
| --- | --- |
| yellow | 0–10 |
| yellow green | 10–40 |
| green | 40–70 |
| blue | 70–up |

EXAMPLE 2

The procedure described in Example 1 above was repeated, except that the solvent used was varied as indicated below in Table 1. Each of these test solutions was mixed with an old, exhausted fat containing a high amount of soap or other alkaline substances so as to render the fat unusable. Table 1 indicates the end color and fat separation obtained in the method employing each such solvent.

TABLE 1

| Solvent | End Color | Fat Separation |
| --- | --- | --- |
| Acetone (Neat) | Yellow | None |
| Acetone containing 10% $H_2O$ | Blue | Good |
| Acetone containig 20% $H_2O$ | Blue | Slow |
| Acetone containing 25% $H_2O$ | Blue | Emulsion (very slow separation) |
| Acetone containing 2% $H_2O$ Ethyl alcohol | Blue | Good |
| containing 5% $H_2O$ Propylene glycol | Green | Good |
| containing 5% $H_2O$ Propylene glycol | Blue | Emulsion |
| containing 10% $H_2O$ | Green | Emulsion |
| Isopropyl alcohol (Neat) | Yellow | Emulsion |
| Isopropyl alcohol containing 4% $H_2O$ | Green | Good |
| Isopropyl alcohol containing 10% $H_2O$ | Green | Emulsion |
| Isopropyl alcohol containing 25% $H_2O$ | Green | Slow |
| Isopropyl alcohol & Acetone (1:1) containing 5% $H_2O$ Propylene glycol | greenish blue | Good |

TABLE 1-continued

| Solvent | End Color | Fat Separation |
| --- | --- | --- |
| & Acetone (1:1) | Green | Emulsion |
| Propylene glycol & Isopropyl Alcohol (1:1) | Green | Very Slow |

The results in Table 1 show that the acetone/$H_2O$ solvent systems are clearly the best of those tested. Other systems such as isopropyl alcohol/4% $H_2O$ solvent system provided good separation but a narrow color change range for the same amount of soap. Also, a number of the solvent systems tested resulted in emulsions under the conditions of the test, and therefore, such systems would require steps to guard against or to break up such emulsions, e.g. salts, additional solvents and/or other emulsion disrupting materials.

EXAMPLE 3

A series of test solutions were prepared in accordance with the procedure of Example 1, except that a different dye was used in each solution. Test solutions containing the following dyes were prepared.
1. Methyl Orange
   pH range Red 3.1–4.4 Orange
2. Congo Red
   pH range Blue 3.0–5.0 Red
3. Bromcresol Green
   pH range Blue 3.8–5.4 Blue
4. Bromcresol Green in alcohol (BPA) solution
5. Bromcresol purple
   pH range yellow 5.2–6.8 purple
6. Chlorphenol red
   pH range yellow 5.2–6.8 red
7. Bromthymol blue
   pH range yellow 6.0–7.6 Blue In the case of Congo red, which is poorly soluble in acetone, alcoholic (both ethanol and isopropanol) solutions were also made.

The test solutions were mixed in accordance with the method of the invention with fats of various known conditions and the color developed in the solvent phase was noted. Table 2 shows the results. Congo red is not shown because the acid (blue) starting form proved to be an insoluble, coagulated solid in all three solutions.

TABLE 2

| Dye Name | Fat Condition/Color Developed | | |
| --- | --- | --- | --- |
|  | Fresh, Unused | used | Old |
| Bromophenol blue (standard) | yellow | pale green | dark blue |
| Methyl Orange | orange | orange | orange |
| Bromocresol Green | yellow | yellow | green |
| Bromocresol Green Alcohol (BPA) sol'n | yellow | yellow | very pale green |
| Bromcresol purple | yellow | yellow | yellow |
| Chlorophenol Red | yellow | yellow | yellow |
| Bromthymol Blue | yellow | yellow | yellow |

The results in Table 2 show that bromophenol blue is the best of the dyes tested in giving a distinct color change for each condition of the fat. Bromcresol green also showed a distinct color change for the oil (higher alkaline content) fat but not for the used fat (intermediate alkaline content). The other dyes showed little or no color change with such fats. Accordingly, the latter dyes would preferably be used with fats containing even high alkaline contents than those tested.

An observation was made that a dye should preferably have an end point color that would not be confused with, or affected by, the color of the fat. A yellow or orange end point color, for instance, might be confusing. Also, having a color foreign to and non-typical for food color, such as blue, seems a good psychological advantage for this kind of testing.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A process for the determination of the amount of alkaline substances in fat, said process comprising the steps of:
   (1) mixing a predetermined amount of a test solution with a predetermined amount of the fat, said test solution comprising pH indicator dye and a solvent; wherein the dye has a visible color change in the pH range of from about 2.5 to about 7.0, the dye is soluble in the solvent and the fat is substantially immiscible with the solvent; wherein the dye and solvent are present in amounts effective to provide said visible color change which depends on the amount of alkaline substances in the fat; and wherein the pH of the test solution is such that the color of the test solution prior to said mixing corresponds to the color of the dye at the lower end of the color change range for the dye;
   (2) allowing the fat and test solution to separate into a solvent phase and a fat phase; and
   (3) determining the amount of alkaline substances in the fat from the color developed in the solvent phase by comparing said developed color to a known standard.

2. A process according to claim 1, wherein said determining step is performed by comparing the color developed in the solvent phase with a set of colors standardized so that each color indicates an amount of alkaline substances in the predetermined amount of the fat and indicates the frying characteristics of the fat.

3. A process according to claim 1 or 2, wherein the dye is selected from the group consisting of bromophenol blue, methyl yellow, congo red, methyl orange, brom-chlorphenol blue, bromcresol green, bromcresol purple, chlorphenol red and bromthymol blue.

4. A process according to claim 1 or 2, wherein said solvent system is a polar organic solvent and an aqueous liquid.

5. A process according to claim 4, wherein said polar organic solvent is selected from the group consisting of acetone, propylene glycol, isopropyl alcohol, ethyl alcohol, and mixtures thereof.

6. A process according to claim 5, wherein the test solution is comprised (1) of dye in an amount effective to provide a visible color change when the test solution is mixed with fats having characteristic amounts of alkaline substances, and (2) of water and polar organic solvent in proportion to each other so as to extract the alkaline substance from the fats and so as to provide a solvent system immiscible with the fats.

7. A process according to claim 1 or 2, wherein the test solution is comprised of from about 0.004 to about 0.008 parts of bromophenol blue per 100 parts of the test solution, from about 2 to about 25 parts of water per 100 parts of the test solution, and from about 75 to about 98 parts of acetone per 100 parts of test solution.

8. A process according to claim 1 or 2, wherein the test solution is comprised of the following components in the following relative amounts: about 0.04 grams of bromophenol blue, about 75 milliliters of water, and the remainder being acetone and small amounts of sodium hydroxide solution and/or hydrogen chloride solution to adjust the pH, made to a total final volume of about 1 liter.

9. A test kit for determining the amount of alkaline substances in fat, said test kit comprising (1) a test solution comprising (a) a pH indicator dye having the visible color change in the pH range of from about 2.5 to about 7.0 and (b) a solvent in which the dye is soluble and with which the fat is substantially immiscible, wherein the dye and solvent are present in amounts effective to provide said visible color change when the test solution is mixed with a fat having a characteristic amount of alkaline substances and wherein the pH of the test solution is such that the color of the test solution corresponds to the color of the dye at the lower end of the color change range for the dye; and (2) a set of colors standardized so that each color of the set corresponds to a color developed when a predetermined amount of fat containing a specified amount of alkaline substances is mixed with a predetermined amount of the test solution.

10. A test kit according to claim 9, wherein the dye is selected from the group consisting of bromophenol blue, methyl yellow, congo red, methyl orange, brom-chlorphenol blue, bromcresol green, bromcresol purple, chlorphenol red, bromthymol blue.

11. A test kit according to claim 9 or 10, wherein said solvent system is a polar organic solvent and an aqueous liquid.

12. A test kit according to claim 11, wherein said polar organic solvent is selected from the group consisting of acetone, propylene glycol, isopropyl alcohol, ethyl alcohol, and mixtures thereof.

13. A test kit according to claim 9, wherein the test solution is comprised of (1) dye in an amount effective to provide a visible color change when the test solution is mixed with a fat having a characteristic amount of alkaline substances and (2) water and polar organic solvent in proportion to each other so as to extract the alkaline substances from the fat and so as to provide a solvent system immiscible with the fat.

14. A test kit according to claim 9, wherein the test solution is comprised of from about 0.004 to about 0.008 parts of bromophenol blue per 100 parts of the test solution, from about 2 to about 25 parts of water per 100 parts of the test solution, and from about 75 to about 98 parts of acetone per 100 parts of test solution.

15. A test kit according to claim 9, wherein the test solution is comprised of the following components in the following relative amounts: about 0.04 grams of bromophenol blue, about 75 milliliters of water, and the remainder being acetone and small amounts of sodium hydroxide solution and/or hydrogen chloride solution to adjust the pH, made to a total final volume of about 1 liter.

* * * * *